United States Patent [19]
Zhang

[11] Patent Number: 5,971,958
[45] Date of Patent: Oct. 26, 1999

[54] INTERLOCKING CATHETER ASSEMBLY

[75] Inventor: John Zhang, Arlington, Mass.

[73] Assignee: Medtronic AVE Inc., Santa Rosa, Calif.

[21] Appl. No.: 08/998,898

[22] Filed: Dec. 29, 1997

Related U.S. Application Data

[63] Continuation of application No. 08/426,151, Apr. 21, 1995, abandoned.

[51] Int. Cl.⁶ .................................................. A61M 5/00
[52] U.S. Cl. ......................... 604/164; 604/165; 604/905; 604/535; 128/912
[58] Field of Search ................................ 604/164, 165, 604/166, 264, 283, 167, 44, 30, 95, 905; 403/315, 320; 128/912

[56] References Cited

U.S. PATENT DOCUMENTS

| | | | |
|---|---|---|---|
| 3,860,006 | 1/1975 | Patel | 128/347 |
| 3,876,234 | 4/1975 | Harms | 604/283 |
| 4,096,860 | 6/1978 | McLaughlin . | |
| 4,192,305 | 3/1980 | Seberg | 604/165 |
| 4,230,123 | 10/1980 | Hawkins, Jr. | 128/772 |
| 4,256,106 | 3/1981 | Shoor | 604/905 |
| 4,431,426 | 2/1984 | Groshong et al. | 604/164 |
| 4,452,473 | 6/1984 | Ruschke | 604/905 |
| 4,609,370 | 9/1986 | Morrison | 604/165 |
| 4,629,450 | 12/1986 | Suzuki et al. | 604/164 |
| 4,653,475 | 3/1987 | Seike et al. | 604/165 |
| 4,682,981 | 7/1987 | Suzuki et al. | 604/158 |
| 4,791,937 | 12/1988 | Wang | 604/164 |
| 4,803,999 | 2/1989 | Liegner | 604/264 |
| 4,838,269 | 6/1989 | Robinson et al. | 604/96 |
| 4,842,592 | 6/1989 | Caggiani et al. | 604/283 |
| 4,946,443 | 8/1990 | Hauser et al. | 604/165 |
| 4,986,814 | 1/1991 | Burney et al. | 604/164 |
| 5,066,285 | 11/1991 | Hillstead | 604/164 |
| 5,098,393 | 3/1992 | Amplatz et al. | 604/167 |
| 5,186,501 | 2/1993 | Mano | 285/89 |
| 5,195,985 | 3/1993 | Hall | 604/195 |
| 5,224,939 | 7/1993 | Holman et al. | 604/283 |
| 5,226,898 | 7/1993 | Gross | 604/283 |
| 5,250,036 | 10/1993 | Farivar | 604/164 |
| 5,334,185 | 8/1994 | Giesy et al. | 604/164 |
| 5,382,255 | 1/1995 | Castro et al. | 403/315 |
| 5,391,152 | 2/1995 | Patterson | 604/165 |
| 5,591,143 | 1/1997 | Trombley, III et al. | 604/283 |
| 5,672,158 | 9/1997 | Okada et al. . | |
| 5,702,374 | 12/1997 | Johnson | 604/283 |
| 5,741,233 | 4/1998 | Riddle et al. . | |
| 5,782,807 | 7/1998 | Falvai et al. . | |

FOREIGN PATENT DOCUMENTS

| | | | |
|---|---|---|---|
| 158030 | 10/1985 | European Pat. Off. . | |
| 3149075 A1 | 8/1983 | Germany | 401/126 |
| 3942000 | 10/1990 | Germany | 401/126 |
| A-43 18101 | 12/1994 | Germany . | |
| A-438101 | 12/1994 | Germany . | |
| WO-A-93/13822 | 7/1993 | WIPO . | |
| WO-A-94/23785 | 10/1994 | WIPO . | |
| WO-A-95/22369 | 8/1995 | WIPO . | |

OTHER PUBLICATIONS

Derwent Abstract of DE–A–4318101 cited in European Search Report.

*Primary Examiner*—Wynn Wood Coggins
*Assistant Examiner*—Sharon Finkel
*Attorney, Agent, or Firm*—Sterne, Kessler, Goldstein & Fox, P.L.L.C.

[57] ABSTRACT

A catheter assembly comprising two elements each having a hub disposed at the proximal end thereof. The hubs are constructed so as to be complementary and rotatably engageable as the result of a plurality of threads disposed on the hubs of the two catheter introducer elements. When the threads of the hubs of the two catheter elements are engaged axial disengagement of the hubs is inhibited. The catheter assembly also comprising a means of securing against accidental rotational disengagement. The size and location of the threads and the rotational securement means permits the catheter assembly to have a lower profile because the distance to the hemostasis gasket is reduced thus permitting easier access to the hemostasis gasket.

23 Claims, 3 Drawing Sheets

INTERLOCKING CATHETER ASSEMBLY

This is a continuation of application Ser. No. 08/426,151 filed Apr. 21, 1995, now abandoned.

BACKGROUND OF THE INVENTION

This invention relates to medical devices for introducing catheters or the like into the body and in particular into blood vessels of the body.

Catheter assemblies provide a reusable conduit for the passage of catheters and other medical devices, e.g., guidewires, through the body flesh into blood vessels or other body passageways. Catheter assemblies are well known in the art. U.S. Pat. No. 5,098,392 granted to Amplatz et al. discloses an introducer assembly having (1) an introducer element consisting of an elongated tubular member defining an introducer sheath and an introducer hub disposed at the proximal end of the introducer sheath which further defines an introducer conduit along a longitudinal axis, and (2) a dilation element having an elongated tubular member defining a dilator having a tapered distal end portion and a dilator hub disposed at the proximal end of the dilator, which is sized so that the dilator may be inserted through the conduit of the introducer hub and introducer sheath and that the dilator tapered distal portion extends beyond the introducer sheath distal end.

Prior to the use of the catheter assembly, a needle is inserted through the body flesh and into a blood vessel, and a guidewire is inserted into the blood vessel through the center passage of the needle. The needle is then removed leaving the guidewire in place. The introducer assembly is then inserted over the guidewire such that the tapered distal portion of the dilator acts to gradually expand the puncture opening to ease the passage of the introducer sheath into the blood vessel. After the introducer sheath has been inserted to a desired depth within the blood vessel, the dilator element is removed from within the introducer element. A catheter can then be inserted through the introducer sheath into the blood vessel. In addition to introducer-dilator assemblies, other catheter assemblies include the combination of an introducer sheath with obturators, sterile sleeves, Tuohy-Borst fittings and the like.

To prevent or minimize the loss of blood or bodily fluid after the catheter assembly is in place, a hemostasis gasket is typically incorporated in the catheter assembly. U.S. Pat. No. 5,098,383 to Amplatz et al. describes such a catheter introducer assembly incorporating a hemostasis gasket. The hemostasis gasket is designed to form a seal after the dilator element or the like has been removed thereby preventing blood or bodily fluid from exiting from the introducer element. After the dilator element has been removed, the catheter which is to be inserted into the blood vessel must be carefully inserted into and guided through and past the hemostasis gasket. As the distance between the proximal end of the hub of the introducer sheath and the hemostasis gasket increases, the gasket becomes less accessible making it increasingly difficult to insert the catheter past the gasket. Moreover, if the catheter being used is of a curved or pigtail design, the difficulty of inserting the catheter through the hemostasis gasket is compounded, and at times requires the user to straighten the catheter with a guidewire prior to insertion.

During the initial insertion of the catheter assembly, the body's resistance to the expansion of the puncture opening exerts forces on the distal portion of the dilator tending to push the distal end of the dilator rearwardly in the proximal direction into the introducer sheath. In order to ensure that the tapered distal portion of the dilator remains extended beyond the blunt distal end of the introducer sheath during the initial insertion of the catheter assembly, the dilator hub is releasably connected to the introducer hub.

Several means for releasably connecting the introducer hub and the hub of the other component of the catheter assembly, e.g., the dilator hub, are known in the prior art. Unfortunately, with some of these prior art designs, the interconnected hubs are prone to becoming accidently disengaged. Moreover, because of the depth of the introducer hub and the distance between the proximal end of the introducer hub and the hemostasis gasket, insertion of certain catheters, particularly those having a curved or pigtail design, into the introducer sheath after the dilator element has been removed, is difficult.

A prior art means for releasably connecting the dilator hub and introducer hub comprises rotatably engaging studs and complementary slots associated with the dilator and introducer hubs. U.S. Pat. No. 4,192,305 to Seberg discloses a catheter placement assembly having a needle and lumen wherein the needle and lumen are mechanically engaged by complementary means associated with the needle and lumen hubs, such as tabs associated with one hub and slots associated with the other hub. U.S. Pat. No. 4,946,443 to Hauser et al. discloses a catheter assembly having a releasable connecting means having a pin or stud associated with one hub that is received by a slot associated with the other hub. Medical assemblies having releasable connecting means of the pin-and-slot type are also disclosed in U.S. Pat. No. 4,609,370 to Morrison; U.S. Pat. No. 4,986,814 to Burney et al.; and U.S. Pat. No. 3,860,006 to Patel. These types of rotatably engaging releasable connecting means do not have a stop means for securely locking the pin within the slot and, therefore, are prone to accidental disengagement through the inadvertent rotation of the dilator hub.

Additionally, U.S. Pat. No. 5,098,393 to Amplatz et al. discloses that the dilator hub and introducer hub may be releasably connected by an axially engaging snap fit or friction fit connection. An axially aligned snap fit connection of the type disclosed in U.S. Pat. No. 5,098,393 is prone to accidental disengagement through the inadvertent application of a transverse force to the proximal end of the dilator hub. Moreover, while the axial alignment of the dilator and introducer hubs is maintained with such a releasable connection, rotational movement between the dilator and introducer hubs is permitted.

Upon an accidental disengagement of the dilator hub and introducer hub during the initial insertion of the catheter assembly, the tapered distal end of dilator would migrate proximally into the introducer sheath and the blunt distal end of the introducer sheath may be forced against the blood vessel. In that event, trauma to the blood vessel and body flesh surrounding the puncture site could result. Such trauma may result in the procedure being reinitiated at another location along the blood vessel or being abandoned altogether. Accidental disengagement of an obturator can result in kinling of the introducer sheath thus preventing further use of the sheath and requiring replacement with a new sheath. Similarly, disengagement of a sterile sleeve from the introducer sheath will compromise the required sterile environment. Further, disengagement of the Tuohy-Borst fitting from the introducer sheath can cause the catheter, which is received by the fitting and within the introducer, to move from its desired position in the patient.

An improved catheter assembly is disclosed in U.S. Pat. No. 5,391,152 to Patterson. This catheter assembly has an improved releasable interlock connection which comprises a first element having a hub with outwardly protruding radial tabs disposed at the distal end of the hub and a second element having a hub with two complementary slots and two interference fit protuberances disposed at the proximal portion of the second element hub A- which rotatably receive and secure the first element tabs. While the catheter assembly disclosed in U.S. Pat. No. 5,391,152 provides an improved "locking mechanism" when Adcompared to the "snap-fit" or "press-fit" interlock designs previously described in the art, the depth of the introducer hub and distance between the proximal end of the introducer hub and the hemostasis gasket makes insertion of a curved or pigtail catheter difficult.

Accordingly, it is an object of the present invention to provide a catheter assembly with a first and second catheter element (e.g., a dilator and an introducer, respectively), each element having a hub with an improved rotatably engageably releasable interlock connection and a rotational securement means which minimizes, and preferably eliminates, the risk of accidental disengagement of both the axial and rotational alignment of the first and second catheter element hubs. It is a further object of this invention to provide a catheter assembly having a reduced distance between the proximal end of the second catheter element hub (e.g., introducer) and the hemostasis gasket thereby permitting the catheter assembly to have a lower profile. A catheter assembly having a lower profile makes it easier, once the first catheter element (e.g., dilator) is inserted into the body and the second catheter element (e.g., introducer) removed, to insert a curved or pigtail catheter into the body through the second catheter element (e.g., introducer).

SUMMARY OF THE INVENTION

The present invention resides in the improvement of providing complementary threads on the component hubs of a catheter assembly, such as between a dilator hub and an introducer hub. These threads permit the user to rotatably engage (e.g., interlock or screw) the component hubs together, thus providing an improved and more secure engagement between the component hubs and thereby preventing accidental axial disengagement. The location of the threads permits the catheter assembly to have a profile which is lower then otherwise possible, thereby permitting easier access to the hemostasis gasket. The component hubs are also provided with a rotational securement means to inhibit accidental rotational disengagement. The rotational securement means can comprise complementary protuberances (e.g., projections, bulges, etc.) and recesses (e.g., depressions, cavities, etc.) so that when the protuberances are in contact with, and seated within, the recesses, accidental rotational disengagement is inhibited.

The catheter assembly of this invention comprises a first catheter element having a hub and a second catheter element having a hub. The hub of the first catheter element has a threaded distal portion and one or more protuberances disposed on the distal end of the hub. The hub of the second catheter element has a proximal threaded portion which is rotatably releasably engageable with the threaded distal portion of the first catheter element. One or more recesses are disposed on the proximal end of the hub of the second catheter element. The protuberances and recesses are complementary in nature. In other words, the protuberances of the first catheter element hub are sized and spaced such that when they are brought into contact with the recesses of the second catheter element hub as a result of the rotational engagement of the threaded portions of the first and second catheter element hubs, the protuberances of the first catheter element hub drop into, and become seated within, the locking recesses of the second catheter element hub. The size and location of the threaded portions of the first and second catheter element hubs combined with the protuberances and recesses permits the catheter assembly to have a lower profile while at the same time preventing accidental axial and rotational disengagement of the first and second catheter elements.

BRIEF DESCRIPTION OF THE DRAWINGS

The invention will be further described, by way of example, with reference to the accompanying drawings wherein.

DETAILED DESCRIPTION OF THE PREFERRED EMBODIMENTS

It should be noted that while the following description will be specifically in the context of an introducer-dilator assembly, the invention is not so limited and is applicable to other catheter assemblies.

Figure 1:
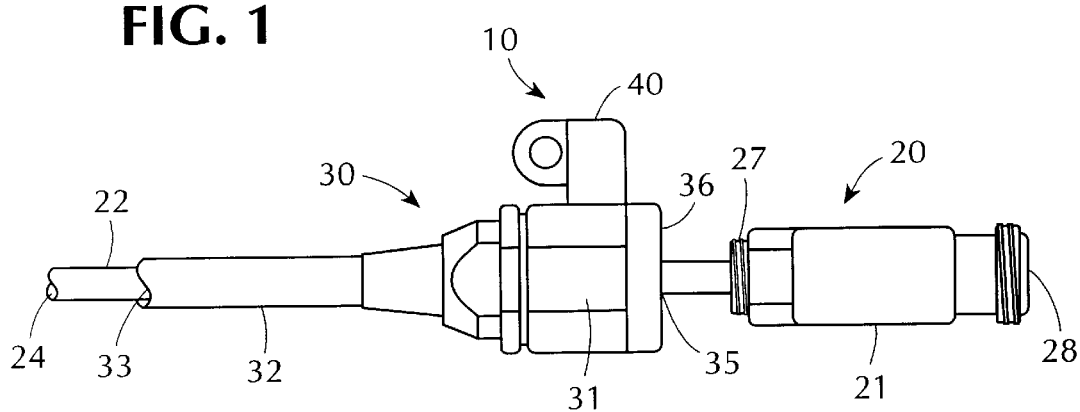
FIG. 1 is perspective view of the proximal end of a catheter assembly made in accordance with this invention.
Figure 6:
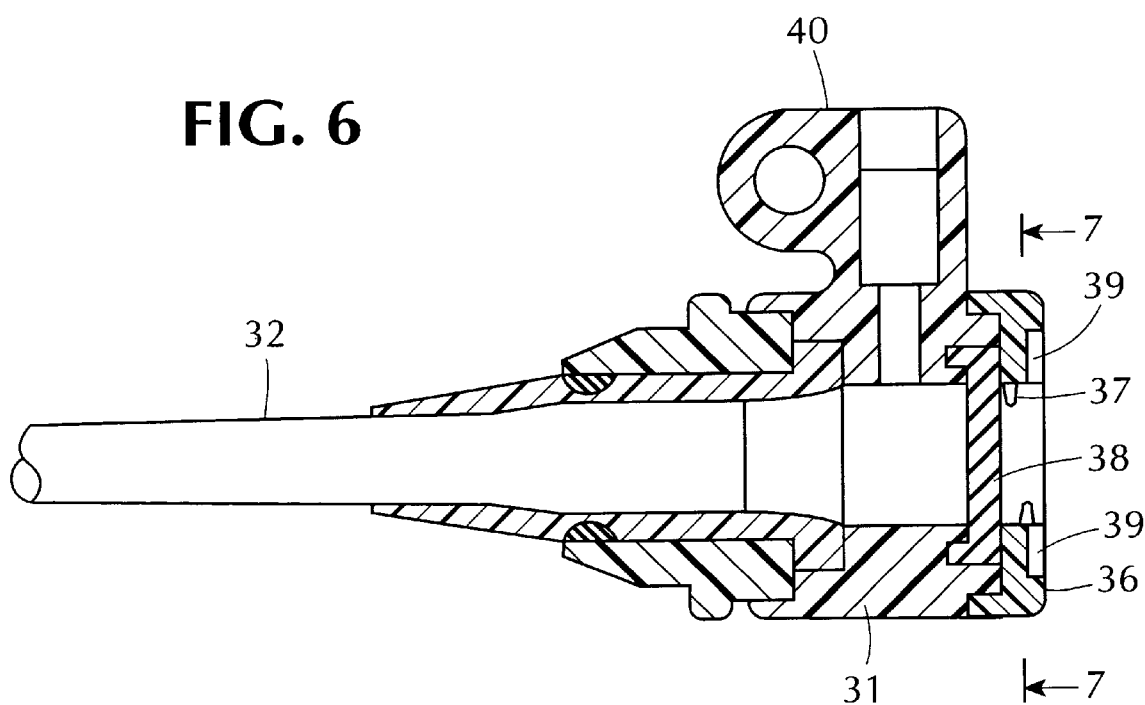
FIG. 6 is a longitudinal sectional view of the proximal end of the introducer of the catheter assembly of FIG. 1.
Figure 7:
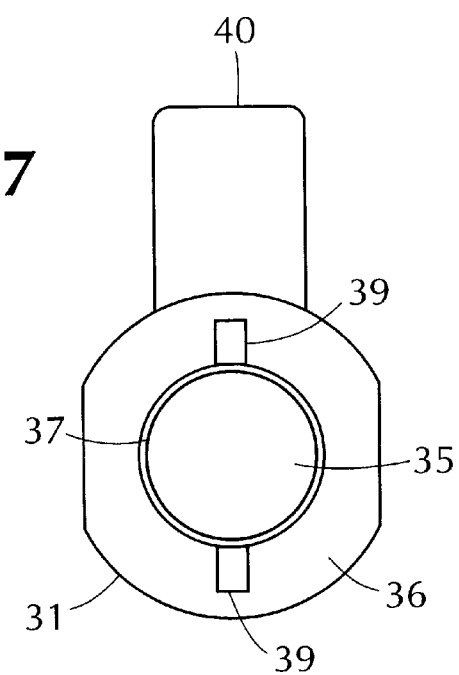
FIG. 7 is a side-elevational view of the introducer hub when viewed along line 5—5 of FIG. 6.

Referring to FIGS. 1 and 6, in a preferred embodiment, catheter assembly 10 comprises a dilator element 20 having a dilator hub 21 having a proximal and distal end and an introducer element 30 having an introducer hub 31 having a proximal and distal end. As will be described below, dilator hub 21 and introducer hub 31 may be rotatably engaged or interlocked. In this preferred embodiment, introducer hub 31 comprises a hemostasis gasket 38 disposed at the proximal end of hub 31 and a sidearm infusion leg 40. Hemostasis gasket 38 limits the leakage of blood or other bodily fluid through introducer element 30. The construction and operation of a hemostasis gasket is well known in the art. See. e.g., U.S. Pat. No. 5,098,393 to Amplatz et al. A tube and stopcock (NOT SHOWN) may be connected to sidearm infusion leg 40. If required, heparin or other chemicals may be directly administered into the blood vessel through sidearm infusion leg 40.

Figure 2:
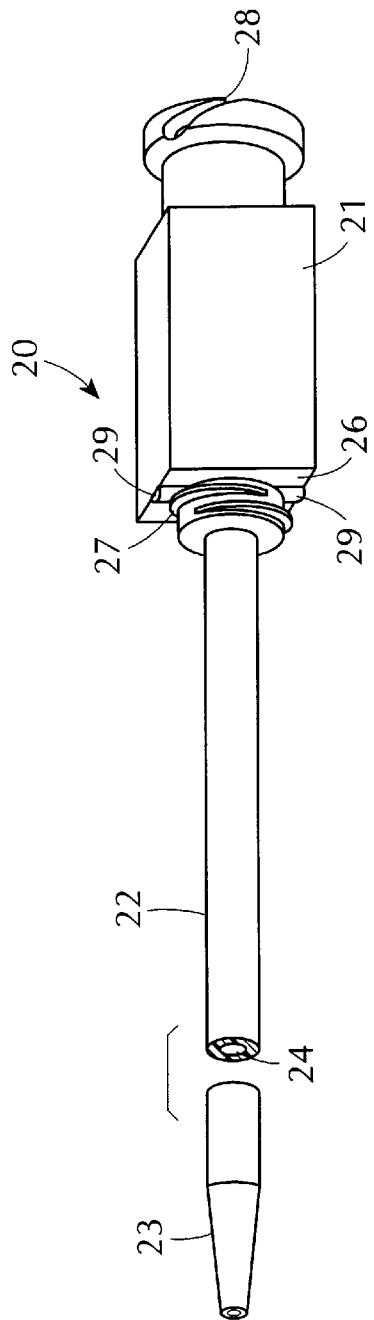
FIG. 2 is an enlarged perspective view of the proximal end of the dilator of the catheter assembly of FIG. 1.

Further referring to FIGS. 1 and 2, in a preferred embodiment, dilator element 20 comprises a dilator 22 having a tapered distal portion 23 and a longitudinal dilator conduit 24 defining a longitudinal axis. Preferably, dilator 22 is formed of a semi-rigid polymer, such as polyvinyl chloride, polypropylene, polyethylene, polyethylene terephthalate, polyurethane, polytetrafluoroethylene, fluoroethylenepropylene or nylon. Dilator 22 is most preferably constructed of polyethylene. Dilator hub 21 is disposed at the proximal end of dilator 22. Dilator hub 21 includes a distal planar surface 26 having a port 28 and a bore at the center of the hub (NOT SHOWN) extending therethrough which communicates with dilator conduit 24. Preferably, dilator hub 21 is formed of a rigid polymer, such as polyethylene or acrylonitrile butadiene styrene (ABS).

Figure 3:
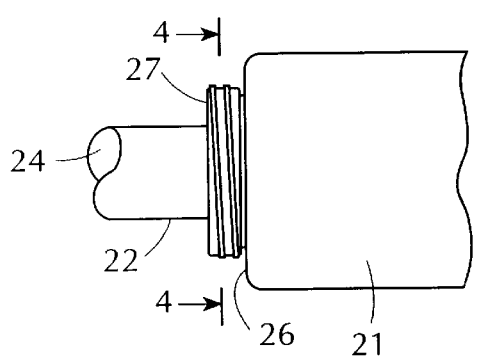
FIG. 3 is a front-elevational view of the proximal end of the dilator hub of this invention.

Referring to FIGS. 2 and 3, in a preferred embodiment, centrally disposed on the distal planar surface 26 of dilator hub 21 is a threaded portion. The threaded portion comprises either outwardly or inwardly protruding threads 27. Threads 27 may be formed of the same materials as dilator hub 21. Threads 27 may be of unitary construction with dilator hub 21 or attached thereto in an integral fashion. In a more preferred embodiment, threads 27 are outwardly protruding or "male."

Figure 4:
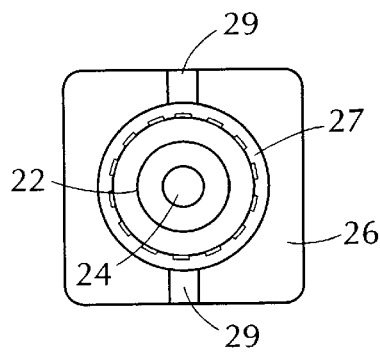
FIG. 4 is a side-elevational view of the dilator hub when view along line 2—2 of FIG. 3.

Referring to FIGS. 2, 3 and 4, in a preferred embodiment, at least one protuberance 29 is disposed on the distal planar surface of dilator hub 21. In a more preferred embodiment, a plurality of protuberances 29 are spaced equally on the distal planar surface 26 of dilator hub 21 along a circumference and extend radially from the center of the bore of hub 21.

Figure 5:
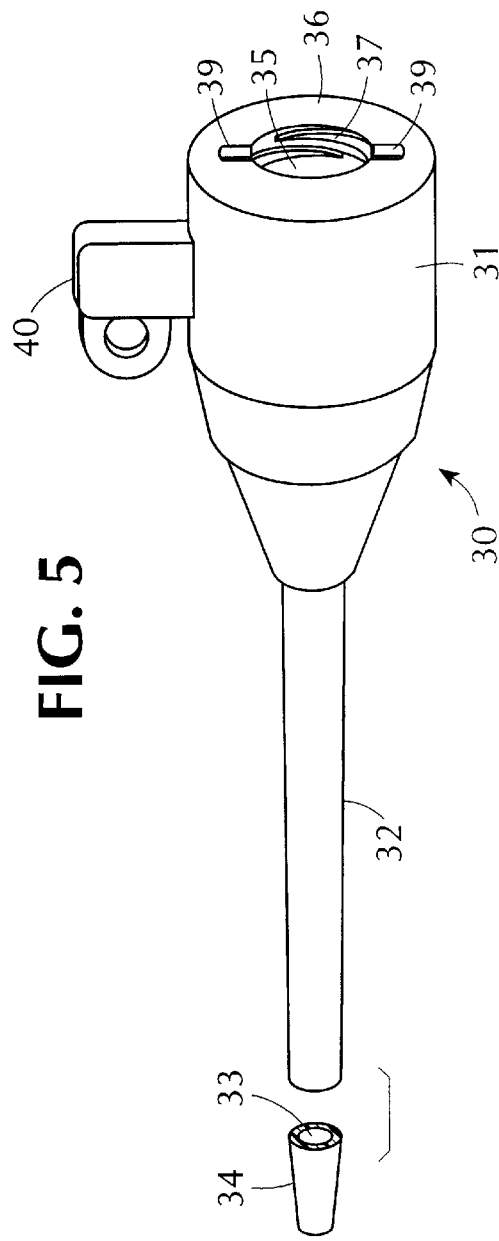
FIG. 5 is an enlarged perspective view of the proximal end of the introducer of the catheter assembly of FIG. 1.

Referring to FIGS. 1 and 5, in a preferred embodiment, introducer element 30 comprises an introducer sheath 32 with a distal portion 34 and a longitudinal introducer conduit 33 defining a longitudinal axis. Typically, the distal portion 34 of introducer sheath 32 is tapered, but it may be blunt. Preferably, introducer sheath 32 is formed of a semi-rigid polymer, such as polyvinyl chloride, polypropylene, polyethylene, polyethylene terephthalate, polyurethane, polytetrafluoroethylene, fluoroethylenepropylene or nylon. Introducer sheath 32 is most preferably constructed of a polyether block amide. Introducer hub 31 is disposed at the proximal end of introducer sheath 32. Introducer hub 31 includes a proximal planar surface 36 and a centrally disposed bore 35 which extends from the proximal planar surface 36 of introducer hub 31 through introducer hub 31 defining an inner surface which communicates with introducer conduit 33. Preferably, introducer hub 31 is formed of a rigid polymer, such as polyethylene or ABS.

Referring to FIGS. 5 and 6, in a preferred embodiment, the inner surface of bore 35 has a proximal threaded portion. The proximal threaded portion comprises either outwardly or inwardly protruding threads 37. Threads 37 are sized and spaced so that they are rotatably engageable with threads 27. Threads 37 may be formed of the same materials as introducer hub 31. Threads 37 may be of unitary construction with introducer hub 31 or attached thereto in an integral fashion. In a more preferred embodiment, threads 37 are inwardly protruding or "female."

Threads 27 and 37 are complementary and are sized and spaced such that they can be engaged when they are rotatably brought into contact. In a more preferred embodiment, threads 27 are double-lead male threads and threads 37 are double-lead female threads and are spaced and sized such dilator hub 21 has to be rotated less than about 180° to engage or disengage dilator hub 21 and introducer hub 31.

Referring to FIGS. S and 7, in a preferred embodiment, at least one recess 39 is disposed on the proximal planar surface 36 of introducer hub :31. In a more preferred embodiment, a plurality of recesses 39 are spaced equally on the proximal planar surface 36 of introducer hub 31 along a circumference and extend radially from bore 35.

In a preferred embodiment, the rotational securement means comprises protuberances 29 and recesses 39 which are complementary and sized and spaced so that when protuberances 29 are brought into contact with the recesses 39 as a result of rotational engagement of threads 27 and 37, protuberances 29 drop into, and become seated within, recesses 39 so that an interference fit results thereby inhibiting accidental rotational disengagement. In a further preferred embodiment, protuberances 29 and recesses 39 are semi-cylindrical in shape. In a more preferred embodiment, two semi-cylindrical protuberances are spaced equally on the planar distal surface 26 of dilator hub 21 along a diameter through the bore of the hub and two complementary semi-cylindrical recesses are spaced equally on the planar proximal surface 36 of introducer hub 31 along a diameter through bore 35.

In an alternative embodiment, the rotational securement means comprises at least one protuberance 29 disposed on the proximal planar surface 36 of introducer hub 31 on a radius from the bore 35 and at least one complementary recess 39 disposed on the distal planar surface 26 of dilator hub 21 on a radius from the bore of hub 21. In a further alternative embodiment, at least one protuberance 29 and at least one recess 39 are disposed on the proximal planar surface 36 of introducer hub 31 and a corresponding number of complementary protuberances 29 and recesses 39 are disposed on the distal planar surface of dilator hub 21.

In another alternative embodiment, the rotational securement means comprises a plurality of threads 27 and 37 sized and spaced so that when threads are rotationally engaged an interference fit between threads 27 and 37 results inhibiting accidental rotational, as well as axial, disengagement of the first and second catheter element hubs. In a further alternative embodiment, the rotational securement means comprises the planar distal surface 26 of dilator hub 21 and the planar proximal surface 36 of introducer hub 31 treated or coated in such a manner so that when distal planar surface 26 and proximal planar surface 36 are brought into contact as a result of rotational engagement of threads 27 and 37, a friction fit results thereby inhibiting accidental rotational disengagement of the first and second catheter element hubs.

In a preferred embodiment, dilator hub 21 and introducer hub 31 may be engaged by bringing threads 27 into contact with threads 37 disposed on the inner surface of the proximal end of introducer bore 35 and rotating dilator hub 21 until threads 27 rotatably engage threads 37. As dilator hub 21 is further rotated so as to more completely rotatably engage threads 27 and 37, protuberances 29 and recesses 39 both axially and rotationally approach and eventually become aligned. Before protuberances 29 come into alignment with recesses 39 as a result of the rotational engagement of threads 27 and 37, protuberances 29 come in contact with the proximal planar surface 36 of introducer hub 31. This increases the resistance to further engagement of threads 27 and 37 and requires an increased torque to overcome the increased resistance. When protuberances 29 drop into, and become seated within, recesses 39 the increased resistance is eliminated and the user is provided with the sense that dilator hub 21 and introducer hub 31 are engaged. When protuberances 29 are seated within recesses 39, an interference fit results. Once protuberances 29 are seated within recesses 39, further rotation is precluded by the combination of the engagement of threads 27 and 37 and the resistance resulting from the interference fit between protuberances 29 and recesses 39.

When threads 27 and 37 are completely engaged, accidental axial disengagement of dilator hub 21 from introducer hub 31 is prevented. Additionally, when protuberances 29 are seated within recesses 39, accidental rotational disengagement is inhibited. When threads 27 and 37 are completely engaged and protuberances 29 are seated within recesses 39, dilator hub 21 and introducer hub 31 can not begin to be axially or rotationally disengaged until the resistance resulting from protuberances 29 being seated within recesses 39 is first overcome. The user in overcoming the resistance resulting from the protuberances 29 being seated in recesses 39 is provided with the sense that the dilator hub 21 and introducer hub 31 are disengaged.

The location of threads 27 and 37, protuberances 29 and recesses 39 allow for a catheter assembly having a lower profile as a result of the reduction in the distance between the proximal surface 36 of introducer hub 31 and hemostasis gasket 38.

Having described the invention in specific detail and exemplified the manner in which it may be carried into practice, it will now be readily apparent to those skilled in the art that innumerable variations, applications, modifications and extensions of the basic principles involved may be made without departing from its scope.

What is claimed is:

1. A catheter assembly comprising:
    a first catheter element having a proximal end, a distal end and a conduit extending between the proximal end and the distal end, the first catheter element having a hub disposed at the proximal end thereof, the hub having a proximal portion, a distal planar surface and a centrally disposed threaded distal portion;
    a second catheter element having a proximal end and a distal end, the second catheter element having a hub disposed at the proximal end thereof, the hub having a proximal planar surface, a threaded proximal portion and a sheath having a bore extending from the proximal end of the second catheter element to the distal end of the second catheter element defining an inner surface into which the conduit of the first catheter element can be inserted to bring the threaded proximal portion of the second catheter element into releasable engagement with the threaded distal portion of the first catheter element; and
    one or more proturbances disposed on the distal planar surface of the first catheter element hub and one or more complimentary recesses disposed on the proximal planar surface of the second catheter element hub for rotatably receiving the proturbances so as to provide an interference fit and inhibit rotational disengagement of the first catheter element hub from the second catheter element hub.

2. The catheter assembly defined in claim 1 wherein the threaded proximal portion of the second catheter element hub is disposed on an inner surface defined by the bore extending from the proximal planar surface of the second catheter element hub toward said distal end of the second catheter element hub.

3. The catheter assembly defined in claim 1 wherein the threaded distal portion of the first catheter element hub comprises outwardly-protruding threads and the threaded proximal portion of the second catheter element hub comprises inwardly-protruding threads.

4. The catheter assembly defined in claim 1 wherein the threads of the first catheter element hub and the threads of the second catheter element hub are double lead threads.

5. The catheter assembly defined in claim 1 wherein the protuberances are spaced equally along a circumference extending radially on the distal planar surface from the centrally disposed threaded distal portion of the first catheter element hub and the recesses are spaced equally along a circumference extending radially on the proximal planar surface from the bore of the second catheter element hub.

6. The catheter assembly defined in claim 5 wherein the protuberances on the distal planar surface of the first catheter element hub are semi-cylindrical in shape and the recesses on the proximal planar surface of the second catheter element are semi-cylindrical in shape.

7. A catheter assembly comprising:
    a first catheter element having a proximal end, a distal end and a conduit extending between the proximal end and the distal end, the first catheter element having a hub disposed at the proximal end thereof, the hub having a proximal portion, a distal planar surface and a centrally disposed threaded distal portion;
    a second catheter element having a proximal end and a distal end, the second catheter element having a hub disposed at the proximal end thereof, the hub having a proximal planar surface, a threaded proximal portion and a sheath having a bore extending from the proximal end of the second catheter element to the distal end of the second catheter element defining an inner surface into which the conduit of the first catheter element can be inserted to bring the threaded proximal portion of the second catheter element into releasable engagement with the threaded distal portion of the first catheter element; and
    one or more proturbances disposed on the proximal planar surface of the second catheter element hub and one or more complimentary recesses disposed on the distal planar surface of the first catheter element hub for rotatably receiving the prolurbances so as to provide an interference fit and inhibit rotational disengagement of the first catheter element hub from the second catheter element hub.

8. The catheter assembly defined in claim 7 wherein the protuberances are spaced equally along a circumference extending radially on the proximal planar surface from the bore of the second catheter element hub and the recesses are spaced equally along a circumference extending radially on the distal planar surface from the centrally disposed threaded distal portion of the first catheter element hub.

9. The catheter assembly defined in claim 7 wherein the threaded proximal portion of the second catheter element hub is disposed on an inner surface defined by the bore extending from the proximal planar surface of the second catheter element hub toward said distal end of the second catheter element hub.

10. The catheter assembly defined in claim 7 wherein the threaded distal portion of the first catheter element hub comprises outwardly-protruding threads and the threaded proximal portion of the second catheter element hub comprises inwardly-protruding threads.

11. The catheter assembly defined in claim 10 wherein the threads of the first catheter element hub and the threads of the second catheter element hub are double lead threads.

12. The catheter assembly defined in claim 8 wherein the proturbances on the proximal planar surface of the second catheter element hub are semi-cylindrical in shape and the recesses on the distal planar surface of the first catheter element hub are semi-cylindrical in shape.

13. A catheter assembly comprising:
    a first catheter element having a proximal end, a distal end and a conduit extending between the proximal end and distal end;
    a first catheter element hub having a distal end and a proximal end, wherein the hub has a center and a distal planar surface;
    the first catheter element hub disposed at the proximal end of the first catheter element;
    a plurality of threads disposed on the distal planar surface of the first catheter element hub;
    one or more proturbances disposed on the distal planar surface of the first catheter element hub;
    a second catheter element having a proximal end and a distal end;

a second catheter element hub having a distal end and a proximal end, wherein the hub has a proximal planar surface and a sheath having a bore extending from the proximal planar surface toward the distal end defining an inner surface into which the conduit of the first catheter element can be inserted;

the second catheter element hub disposed at the proximal end of the second catheter element;

a plurality of threads disposed on the inner surface of the proximal end of the bore wherein the threads are sized and spaced so as to be rotatably engageable with the threads of the first catheter element hub so that when the threads are engaged, axial disengagement of the first and the second catheter elements is inhibited; and one or more recesses disposed on the proximal planar surface of the second catheter element hub complementary with the protuberances disposed on the distal planar surface of the first catheter element hub so that when the recesses and protuberances rotatably come into contact an interference fit results inhibiting rotational disengagement of the first and second catheter element hubs.

14. The catheter assembly defined in claim 13 wherein the protuberances are disposed equally along a circumference extending radially on the distal planar surface from the center of the first catheter element hub and the recesses are disposed equally along a circumference extending radially on the proximal planar surface from the bore of the second catheter element hub.

15. The catheter assembly defined in claim 13 wherein the threads of the first catheter element hub are outwardly protruding and the threads of the second catheter element hub are inwardly protruding.

16. The catheter assembly defined in claim 13 wherein the threads of the first catheter element hub and the threads of the second catheter element hub are double lead threads.

17. The catheter assembly defined in claim 13 wherein the second catheter element further includes an introducer sheath.

18. The catheter assembly defined in claim 13 wherein the first catheter element further includes a dilator.

19. The catheter assembly defined in claim 13 wherein the first catheter element further includes an obturator.

20. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath, the hub having a proximal planar surface with a bore extending from the proximal planar surface toward the distal end defining an inner surface and further defining an introducer conduit therethrough;

a plurality of inwardly protruding threads disposed along the inner surface of the proximal end of the bore;

two recesses disposed equally on the proximal planar surface of the introducer hub along a circumference and extending radially on the proximal planar surface from the bore of the introducer hub;

a dilator comprising an elongated tubular element having a distal end and a proximal end, the dilator defining a longitudinal dilator conduit, the dilator having a tapered distal portion, the dilator being receivable through the introducer conduit so that the tapered distal portion of the dilator extends beyond the distal end of the introducer sheath;

a dilator hub having a center, a distal end and a proximal end, the dilator hub disposed at the proximal end of the dilator, the dilator having a distal planar surface and further defining a dilator conduit therethrough;

a plurality of outwardly protruding threads disposed on the distal planar surface of the dilator hub sized and spaced so as to rotatably engage and interlock with the inwardly protruding threads of the introducer hub so that when the threads are engaged axial disengagement of the introducer dilator hubs is inhibited; and two protuberances disposed equally on the distal planar surface of the dilator hub along a circumference and extending radially from the center of the dilator hub, the protuberances sized and spaced so that the protuberances are capable of being rotatably received by the recesses of the introducer hub so that when the protuberances come into contact with the recesses an interference fit results inhibiting rotational disengagement of the introducer and dilator hubs.

21. A catheter assembly defined in claim 6 wherein the threads of the introducer hub and dilator hub are double lead threads.

22. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath, said hub having a proximal planar surface with a bore extending from the proximal planar surface toward the distal end defining an inner surface and further defining an introducer conduit therethrough;

a plurality of inwardly protruding threads disposed along the inner surface of the proximal end of the bore;

two recesses disposed equally on the proximal planar surface of introducer hub along a circumference and extending radially on the proximal planar surface from the bore of the introducer hub;

an obturator comprising an elongated tubular element having a distal end and a proximal end;

an obturator hub having a center, a distal end and a proximal end, the obturator hub disposed at the proximal end of the obturator, the obturator having a distal planar surface with a center;

a plurality of outwardly protruding threads disposed on the distal planar surface of the obturator hub sized and spaced so as to rotatably engage and interlock the said inwardly protruding threads of the introducer hub so that when the threads are engaged axial disengagement of the introducer and obturator hubs is inhibited; and two protuberances disposed equally on the distal planar surface of the obturator hub along a circumference and extending radially from the center of the obturator hub, the protuberances sized and spaced so that the protuberances are capable of being rotatably received by the recesses of the introducer hub so that when the protuberances come into contact with the recesses an interference fit results inhibiting rotational disengagement of the introducer and obturator hubs.

23. A catheter assembly defined in claim 22 wherein the threads of the introducer hub and obturator hub are double lead threads.

* * * * *

UNITED STATES PATENT AND TRADEMARK OFFICE
CERTIFICATE OF CORRECTION

PATENT NO. : 5,971,958
DATED : October 26, 1999
INVENTOR(S) : Zhang

Page 1 of 1

It is certified that error appears in the above-identified patent and that said Letters Patent is hereby corrected as shown below:

Column 7,
Lines 36 and 40, please delete "proturbances" and insert -- protuberances -- therefor.
Line 55, please delete "claim 1" and insert -- claim 3 -- therefor.

Column 8,
Lines 20 and 50, please delete "proturbances" and insert -- protuberances -- therefor.
Line 24, please delete "prolurbances" and insert -- protuberances -- therefor.

Column 10,
Line 20, please delete "claim 6" and insert -- claim 20 -- therefor.

Signed and Sealed this

Eighteenth Day of December, 2001

Attest:

Attesting Officer

JAMES E. ROGAN
*Director of the United States Patent and Trademark Office*